(12) United States Patent
Diedrich et al.

(10) Patent No.: US 8,173,703 B2
(45) Date of Patent: May 8, 2012

(54) SKIN TREATMENTS WITH CARBOXYLIC ACID-SUBSTITUTED IDEBENONE DERIVATIVES

(75) Inventors: Falko Diedrich, Kaufungen (DE); Birgit Neudecker, Fuldatat-Rothwesten (DE); Eberhard Wieland, Stuttgart (DE); Joseph A. Lewis, II, Chesterfield, VA (US); Joseph C. DiNardo, Vesuvius, VA (US); Andrew S. Thompson, Mountainside, NJ (US); James Alan Kerschen, Somerset, NJ (US); Peter C. Wade, Somerset, NJ (US)

(73) Assignee: Elizabeth Arden, Inc., New York, NY (US)

( * ) Notice: Subject to any disclaimer, the term of this patent is extended or adjusted under 35 U.S.C. 154(b) by 245 days.

(21) Appl. No.: 12/574,135

(22) Filed: Oct. 6, 2009

(65) Prior Publication Data

US 2010/0086494 A1 Apr. 8, 2010

Related U.S. Application Data

(60) Provisional application No. 61/103,043, filed on Oct. 6, 2008.

(51) Int. Cl.
*A61K 31/225* (2006.01)
*A61K 8/00* (2006.01)

(52) U.S. Cl. .......................................... 514/548; 424/59
(58) Field of Classification Search ........................ None
See application file for complete search history.

(56) References Cited

U.S. PATENT DOCUMENTS 6,756,045 B1   6/2004   Neudecker et al.

OTHER PUBLICATIONS

Green et al.; "Childhood exposure to ultraviolet radiation and harmful skin effects: Epidemiological evidence"; 2011; Progress in Biophysics and Molecular Biology; xxx (E-pub ahead of print): 1-7.*
Villalba et al.; "Therapeutic use of coenzyme Q10 and coenzyme Q10-related compounds and formulations"; 2010; Expert Opin. Investig. Drugs; 19(4): 535-554.*
Suggitt, et al.; "50 Years of Preclinical Anticancer Drug Screening: Empirical to Target-Driven Approaches"; 2005; Clinical Cancer Research; 11: 971-981.*
Ikehata et al.; "The Mechanisms of UV Mutagenesis"; 2011; J. Radiat. Res.; 52:115-125.*
International Preliminary Report on Patentability. PCT/US2009/059673. Apr. 21, 2011.
Pignatello, R. et al. A calorimetric 2-21 evaluation of the interaction of amphiphilic prodrugs of idebenone with a biomembrane model. Journal of Colloid and Interface Science, Academic Press, New York, NY, US LNKDDOI: IO,1016/J.JCIS.2006,02.023, vol. 299, No. 2, Jul. 15, 2006, pp. 626-635.
International Search Report. PCT/US2009/059673. Apr. 15, 2010.

* cited by examiner

*Primary Examiner* — Timothy Thomas
(74) *Attorney, Agent, or Firm* — Kalow & Springut LLP; Scott D. Locke, Esq.

(57) ABSTRACT

The present invention relates to novel carboxylic acid-substituted idebenone derivatives, skin treatment compositions containing these carboxylic acid-substituted idebenone derivatives, methods of treating skin changes by topical application of these carboxylic acid-substituted idebenone derivatives, and their methods of synthesis. The carboxylic acid-substituted idebenone derivatives of the present invention are unexpectedly effective in treating skin, particularly with respect to skin tolerance. When included in a topical composition, the carboxylic acid-substituted idebenone derivatives of the present invention have an antioxidant effect that is useful in treating a skin change.

5 Claims, No Drawings

SKIN TREATMENTS WITH CARBOXYLIC ACID-SUBSTITUTED IDEBENONE DERIVATIVES

This application claims the benefit of priority to U.S. Provisional Patent Application No. 61/103,043 filed Oct. 6, 2008, which is hereby incorporated by reference in its entirety.

FIELD OF THE INVENTION

The present invention relates to topical dermatological compositions containing an effective amount of a carboxylic acid-substituted idebenone derivative. In particular, the invention relates to compositions that provide effective protection from damaging oxidation processes in the skin leading to skin changes, and also provide protection for the compositions themselves (including, for example, the constituents of cosmetic compositions containing these carboxylic acid-substituted idebenone derivatives) from damaging oxidation processes. Furthermore, the carboxylic acid-substituted idebenone derivatives of the present invention show significant skin tolerance (i.e., non-irritation), support vesicular breathing and cellular respiration, contribute to stabilization of mitochondrial membranes, and promote the regeneration and vitality of skin cells.

BACKGROUND

Skin is exposed to damage resulting from various sources, including both environmental factors and biochemical processes. Oxidative processes damage proteins, lipids, and other cellular components necessary to maintain the health and appearance of skin, resulting in skin changes, such as skin aging (e.g., age spots), hyperpigmentation, UV damage, lines, wrinkles, uneven skin texture (e.g., cellulitis), etc. Oxidative damage to the skin and its more detailed causes are listed in Miyachi, Y: "Skin diseases associated with oxidative injury," Fuchs J, Packer L (eds.), OXIDATIVE STRESS IN DERMATOLOGY, Marcel Dekker, New York, pp. 323-331 (1993).

The damaging effects of the UV part of solar radiation on the skin are generally known. While rays having a wavelength which is less than 290 nm (the UVC range), are absorbed by the ozone layer in the earth's atmosphere, rays in the range between 290 nm and 320 nm (the UVB range), cause an erythema, simple sunburn or even more or less severe burns. The narrower range around 308 nm is given as a maximum for erythema activity of sunlight. For protection against UVB radiation, numerous compounds are known, in which they are derivatives of 3-benzylidene camphor, 4-aminobenzoic acid, cinnamic acid, salicylic acid, benzophenone and also 2-phenylbenzimidazole. Also, for the range between about 320 nm and about 400 nm (the UVA range) it is important to have filter substances available, since its rats may cause reactions in light-sensitive skin. It has been proven that UVA radiation leads to damage of the elastic and collagenic fibres of the connective tissue, which allows the skin to age prematurely, and that it is to be regarded as a cause of numerous phototoxic and photoallergic reactions. The damaging influence of UVB radiation may be amplified by UVA radiation. It has also been proven that consumption of lipophilic antioxidants, for example, alpha-tocopherol, is triggered in the skin by UVA and UVB radiation (Thiele et al., J. Invest. Dermatol. 100, p. 756 ff. (1998)).

Further, UV radiation is ionizing radiation. Hence, there is the risk that ionic species are produced on UV exposure, which then in turn are able to intervene oxidatively in the biochemical processes.

For protection against the rays of the UVA range, certain derivatives of dibenzoylmethane have therefore been used, the photostability of which (Int. J. Cosm. Science 10, 53 (1988)) is not provided to an adequate extent. UV radiation, however, may also lead to photochemical reactions, wherein then the photochemical reaction products intervene in the skin mechanism.

Predominantly such photochemical reaction products are free radical compounds, for example hydroxyl radicals. Also, undefined free radical photoproducts, which are produced in the skin itself, may trigger uncontrolled side reactions due to their high reactivity. Singlet oxygen, a non-free radical excited state of the oxygen molecule, however, may occur in UV irradiation, short-lived epoxides and many others. Singlet oxygen, for example, is characterized with respect to the normally existing triplet oxygen (free radical base state) by increased reactivity. Nevertheless, excited, reactive (free radical) triplet states of the oxygen molecule also exist. Furthermore, there is the occurrence of lipid peroxidation products, such as hydroperoxides and aldehydes, wherein first in turn free radical chain reactions may be triggered and to which overall cytotoxic properties have to be ascribed (Michiels and Ramacle, Toxicology, 66, 225 ff. (1990)). Lipid peroxidation is an oxidative process that degrades lipids, wherein free radicals steal electrons from the lipids in cell membranes, causing oxidative stress and cell damage.

Light-sensitive skin includes the disorder photodermatoses (photosensitive eruptions). Further designations for the polymorphic light-dermatosis are PLD, PLE, Mallorca Acne and a plurality of further designations, as are given in the literature (e.g., A. Voelckel et al., Zentralblatt Hautund Geschlechtskrankheiten (1989), 156, p. 2).

Erythematous skin symptoms also occur as concomitant symptoms in certain skin diseases or skin irregularities. For example, the typical rash in the clinical picture of acne is regularly reddened to a greater or lesser extent.

In order to prevent these reactions, additional antioxidants and/or free radical absorbers/scavengers may be incorporated in cosmetic or dermatological formulations. Antioxidants are substances that scavenge free radicals and prevent oxidation processes or prevent the auto-oxidation of fats containing unsaturated compounds. Antioxidants used in the field of cosmetics and pharmacy are, for example, alpha-tocopherol, in particular in the form of alpha-tocopheryul acetate, sesamol, colic acid derivatives, butylhydroxy anisole, butylhydroxy toluene, and idebenone. Antioxidants are mainly used as protective substances against the decay of the compositions containing them. However, it is known that undesirable oxidation processes may also occur in the human and animal skin. Such processes play a considerable part in skin aging. Thus, antioxidants and/or free radical absorbers may additionally be incorporated into cosmetic formulations to treat or prevent damage caused by oxidative and degenerative biochemical processes. It has been proposed to use vitamin E (U.S. Pat. Nos. 4,144,325 and 4,248,861), a substance having known anti-oxidative action in sunscreen formulations, but even here the action achieved remains far below that hoped for. Tocopherol (a vitamin E antioxidant), for example, degrades to form pro-oxidative products.

Idebenone (6-(10-hydroxydecyl)-2,3-dimethoxy-5-methyl-1,4-benzoquinone) has been used previously to treat skin changes. For example, U.S. Pat. No. 6,756,045, describes the use of idebenone as a topical composition for treating skin changes.

SUMMARY OF THE INVENTION

The present invention relates to compounds of Formula I: 1.

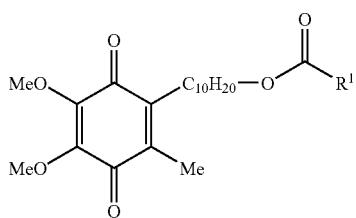

Formula I wherein $R^1$ is a $C_{2-22}$ straight or branched sugar acid, and wherein two or more hydroxy groups on the sugar acid are each independently substituted with a $C_{1-22}$ carboxylic acid.

The present invention also relates to a method of preparing a compound of general Formula I by coupling a corresponding di-, tri-, or poly-carboxylic acid functionalized sugar acid to idebenone. For example, a method of preparing idebenone dipalmitoyl glycerate includes the steps of: subjecting benzyl acrylate to a dihydroxylation reaction to form benzyl 2,3-dihydroxypropanoate; reacting the benzyl 2,3-dihydroxypropanoate with palmitoyl chloride to form 3-(benzyloxy)-3-oxopropane-1,2diyl dipalmitate; reacting the 3-(benzyloxy)-3-oxopropane-1,2diyl dipalmitate with ethyl acetate to form 2,3-bis(palmitoyloxy)propanoic acid; and reacting the 2,3-bis(palmitoyloxy)propanoic acid with idebenone to form idebenone dipalmitoyl glycerate.

The present invention also relates to a composition comprising a compound of general Formula I and at least one additive.

Further, the present invention relates to a method of treating a skin change, comprising topically administering a composition comprising a therapeutically effective amount of a compound of general Formula I to a subject in need thereof.

DETAILED DESCRIPTION

The carboxylic acid-substituted idebenone derivatives of the present invention are antioxidants and provide a significant benefit in treating and preventing skin damage and unwanted skin changes caused by oxidative and degenerative processes. The inventors have surprisingly discovered that compositions prepared with carboxylic acid-substituted idebenone derivatives of the present invention provide a major improvement over comparable compositions prepared with underivatized idebenone or with underivatized idebenone substituted with a monocarboxylic acid. Notably, neither underivatized idebenone nor underivatized idebenone substituted with a monocarboxylic acid include a sugar acid attached to idebenone, as in the compounds of the present invention. Rather, the carboxylic acid-substituted idebenone derivatives of the present invention are surprisingly and significantly more effective in treating skin changes and show significantly increased skin tolerance. Consequently, these compounds provide a major advance and improvement in skin treatment compositions.

For example, delivery of the active ingredient (idebenone) is enhanced because the present carboxylic acid-substituted idebenone derivatives increase skin permeability by virtue of the presence of carboxylic acids (particularly di-, tri-, or poly-fatty acids) that render the compound more soluble across the stratum corneum lipid bi-layers of the skin that are composed of ceramides, cholesterol, and essential fatty acids. Delivery of the active ingredient is also enhanced because the present carboxylic acid-substituted idebenone derivatives increase cell permeability, which occurs because cell membranes are composed of fat soluble lipids. Additionally, compositions prepared with the present carboxylic acid-substituted idebenone derivatives are able to provide a slow release therapy as the compound hydrolyzes in the skin over time.

All of the foregoing advances associated with carboxylic acid-substituted idebenone derivatives of the present invention (i.e., reduced skin irriation, reduced inflammation, increased skin permeability, increased cell permeability, and slow release therapy) lead to improved skin conformity, and allow the skin treatment compositions of the present invention to be used on more skin types, more skin conditions, and on more areas of the body than has been effectively feasible using comparable compositions prepared with underivatized idebenone or underivatized idebenone substituted with a monocarboxylic acid. Moreover, the carboxylic acid-substituted idebenone derivatives of the present invention have been found to be more hypo-allergenic and achieve improved efficacy in treating skin damage (e.g., brown pigmentation) when compared with underivatized idebenone or underivatized idebenone substituted with a monocarboxylic acid.

The carboxylic acid-substituted idebenone derivatives of the present invention may be prepared and used in topical compositions for the treatment of skin changes. The compositions of the invention may include other components or additives, such as glycosaminoglycans and their salts, in particular hyaluronic acids having a molecular weight of 1 to 1,000,000 and their salts, or hyaluronidase inhibitors, such as inter-alpha-trypsin inhibitor. The compositions of the invention can be used to treat or prevent a wide variety of skin changes (e.g., erythematous), inflammatory, allergic or autoimmune-reactive symptoms (e.g., dermatoses), skin changes in light-sensitive skin (e.g., photodermatoses), hyperpigmentation (e.g., age spots), and damaging effects of the UV part of solar radiation on the skin.

The present invention comprises compounds of Formula I:

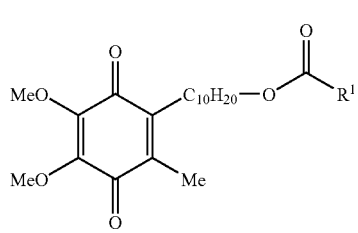

Formula I wherein $R^1$ is a $C_{2-22}$ straight or branched sugar acid, and wherein two or more hydroxy groups on the sugar acid are each independently substituted with a $C_{1-22}$ carboxylic acid. Preferably, 2, 3, 4, or 5 hydroxy groups of the sugar acid are each independently substituted with a $C_{1-22}$ carboxylic acid. Preferred compounds of the present invention may also include fewer hydroxy groups substituted with longer chain carboxylic acids or more hydroxy groups substituted with shorter chain carboxylic acids.

Suitable carboxylic acids for use in the present invention include monocarboxylic acids or polycarboxylic acids. The carboxylic acids may be straight chained, saturated carboxylic acids (e.g., formic acid, acetic acid, propionic acid, butyric acid, valeric acid, caproic acid, enanthic acid, caprylic acid, pelargonic acid, capric acid, lauric acid, palmitic acid, and stearic acid) or short-chain unsaturated monocarboxylic acids (e.g., acrylic acid).

Preferably, carboxylic acids of the present invention are fatty acids (e.g., conjugate fatty acids, medium to long-chain saturated and unsaturated monocarboxylic acids, such as docosahexaenoic acid, and eicosapentaenoic acid). Carboxylic acids for use in the present invention also include amino acids, keto acids (e.g., pyruvic acid, acetoacetic acid), aromatic carboxylic acids (e.g., benzoic acid, salicylic acid), dicarboxylic acids (e.g., aldaric acid, oxalic acid, malonic acid, malic acid, succinic acid, glutaric acid, adipic acid, maleic acid, fumaric acid, phthalic acid, etc.), tricarboxylic acids (e.g., citric acid, isocitric acid, aconitic acid, propane-1,2,3-tricarboxylic acid (e.g., tricarballylic acid, carballylic acid)), alpha hydroxycarboxylic acids (e.g., glycolic acid, lactic acid, hydroxyacrylic acid, oxybutyric acid, glyceric acid, malic acid, tartaric acid and citric acid), and hyaluronic acid.

"Sugar acid" is defined as a straight or branched, saturated or unsaturated, substituted or unsubstituted $C_{2-22}$ (preferably $C_{2-10}$, more preferably $C_{2-5}$) alkyl group substituted with two or more carboxyl groups wherein the hydroxy functional groups of two or more carboxyl groups are each independently substituted with a $C_{1-22}$ carboxylic acid (preferably $C_{14-20}$, more preferably $C_{15-18}$). "Branched" refers to one or more lower alkyl groups such as methyl, ethyl, or propyl attached to a linear alkyl chain. Preferably, 2, 3, 4, or 5 hydroxy groups on the sugar acid are each independently substituted with a $C_{1-22}$ carboxylic acid.

The inventors have found that compounds of the present invention are surprisingly effective in treating skin changes because they provide the added benefits of reduced skin irriation, reduced inflammation, increased skin permeability, increased cell permeability, and slow release therapy.

In a preferred embodiment, the compound of Formula I is 3-oxo-3-(9-(2,4,5-trimethyl-3,6-dioxocyclohexa-1,4-dienyl)monyloxy)propane-1,2-diyl dipalmitate (idebenone dipalmitoyl glycerate), wherein $R^1$ is a $C_2$ sugar acid wherein two hydroxy groups are each independently substituted with a $C_{16}$ carboxylic acid. The structure of idebenone dipalmitoyl glycerate is shown below:

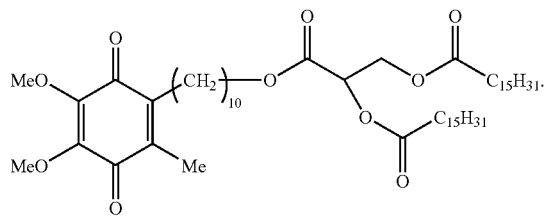

In another embodiment, the present invention includes topical compositions comprising carboxylic acid-substituted idebenone derivatives (e.g., idebenone dipalmitoyl glycerate or another compound of Formula I) and at least one additive. The composition may be provided in a form selected from creams, lotions, solutions, sera, anhydrous preparations, emulsions, microemulsions, multiple emulsions, gels, solid sticks, ointments, and aerosols. The at least one additive may be selected from surfactants, cosmetic auxiliaries, pigments, UVA filters, UVB filters, propellants, thickening agents, emulsifiers, solvents, water, antioxidants, perfumes, dyestuffs, deodorants, antimicrobial materials, back-fatting agents, complexing and sequestering agents, pearlescent agents, plant extracts, vitamins, and combinations thereof.

In another embodiment, the present invention relates to a method of making carboxylic acid-substituted idebenone derivatives of general Formula I. In general, compounds of the present invention are made by syntheses that include a reaction well known in the art as a Fischer esterification, by which a carboxylic acid reacts with an alcohol to form an ester, as generically illustrated below:

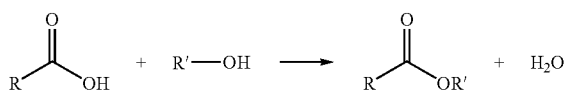

For example, a compound of general Formula I (wherein $R^1$ is a $C_{2-22}$ straight or branched sugar acid, and wherein two or more hydroxy groups on the sugar acid are each independently substituted with a $C_{1-22}$ carboxylic acid) may be made by coupling a di-, tri-, or poly-carboxylic acid functionalized sugar acid to idebenone.

In one embodiment, compounds of the present invention may be synthesized by the following reaction scheme:

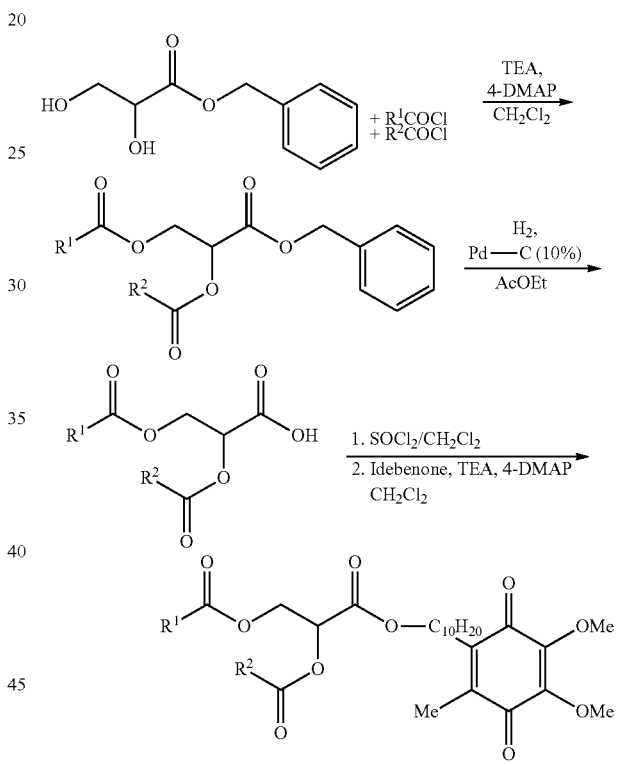

where $R^1$ and $R^2$ are as defined above.

For example, idebenone dipalmitoyl glycerate may be prepared by a method comprising the steps of (a) subjecting benzyl acrylate to a dihydroxylation reaction to form benzyl 2,3-dihydroxypropanoate; (b) reacting the benzyl 2,3-dihydroxypropanoate with palmitoyl chloride to form 3-(benzyloxy)-3-oxopropane-1,2diyl dipalmitate; (c) reacting the 3-(benzyloxy)-3-oxopropane-1,2diyl dipalmitate with ethyl acetate to form 2,3-bis(palmitoyloxy)propanoic acid; and (d) reacting the 2,3-bis(palmitoyloxy)propanoic acid with idebenone to form idebenone dipalmitoyl glycerate.

In yet another embodiment, the present invention relates to a method of treating or preventing the worsening of a skin change or (e.g., skin aging (e.g., age spots, wrinkling, fine lines), hyperpigmentation (e.g., age spots), UV damage, erythematous, cellulitis, inflammatory symptoms, photodamage, photoreactions, etc.) comprising topically administering an effective amount of a carboxylic acid-substituted idebenone derivative of the present invention (e.g., idebenone dipalmitoyl glycerate) to a patient in need thereof. Compositions of the present invention may be used to reduce, if not completely prevent, damage to the skin caused by oxidative influence, and cause a regenerating and vitalizing effect on aging, stressed, or damaged skin by supporting vesicular breathing, stabilization of mitochondrial membranes, and anti-apoptotic properties. These methods of treating a skin change comprise topically administering a composition of the present invention (containing a carboxylic acid-substituted idebenone derivative, particularly of Formula I, and preferably idebenone dipalmitoyl glycerate) to a subject in need thereof, wherein the carboxylic acid-substituted idebenone derivative is present in a therapeutically effective amount. These compositions may contain a carboxylic acid-substituted idebenone derivative in a therapeutically effective amount of 0.0001 wt % to 30 wt %, preferably 0.05 wt % to 5 wt %, more preferably 0.1 wt % to 2.0 wt %, based on the total weight of the composition. The skin change may be selected from skin aging, hyperpigmentation, skin changes caused by UV damage, and skin changes that comprise erythematous symptoms.

The compounds of Formula I may be used in topical cosmetic or dermatological compositions and act as antioxidants and free radical absorbers/scavengers. These compounds provide better prevention of damage to lipids, DNA, and proteins and also better prevent skin aging and wrinkle formation. Examples of carboxylic acid-substituted idebenone derivatives of Formula I include, but are not limited to: idebenone dipalmitoyl glycerate, idebenone dimyristoyl glycerate, idebenone dioleyl glycerate, idebenone dilinoleyl glycerate, idebenone dieicosapentaenyl glycerate, idebenone dierucyl glycerate, and other idebenone sugar acid derivatives with two carboxylic acid substitutions, as well as idebenone trimyristoyl trihydroxypropanoate, idebenone trioleyl trihydroxypropanoate, idebenone trilinoleyl trihydroxypropanoate, idebenone trieicosapentaenyl trihydroxypropanoate, and idebenone trierucyl trihydroxypropanoate, and other idebenone sugar acid derivatives with three carboxylic acid substitutions, etc.

Compositions comprising carboxylic acid-substituted idebenone derivatives of the present invention protect the skin against photo-reactions and prevent or treat inflammatory reactions. It could not have been foreseen that topical application of the carboxylic acid-substituted idebenone derivative compounds, such as those that contain di-, tri-, or poly-fatty acids, would result in significantly less skin irritation or inflammation than similar compositions containing underivatized idebenone or underivatized idebenone substituted with a monocarboxylic acid (see Examples). This was a surprising result. The compositions of the present invention also exhibit greater stability than other skin care active ingredients, such as vitamin C and vitamin E. By exhibiting significantly increased skin tolerance, the carboxylic acid-substituted idebenone derivatives of the present invention are surprisingly and significantly more effective in treating skin changes than similar compositions containing underivatized idebenone or underivatized idebenone substituted with a monocarboxylic acid.

The compositions of the present invention may contain at least one additive. Suitable additives include, but are not limited to, surfactants, cosmetic auxiliaries, pigments, UVA filters, UVB filters, propellants, thickening agents, emulsifiers, solvents (e.g., alcoholic solvents), water, antioxidants, perfumes, dyestuffs, deodorants, antimicrobial materials, back-fatting agents, complexing and sequestering agents, pearlescent agents, plant extracts, vitamins, active ingredients, and/or derivatives and combinations thereof.

Pro-oxidative degradation products do not occur when using carboxylic acid-substituted idebenone derivatives of Formula I. The use of carboxylic acid-substituted idebenone derivatives as antioxidants and their use for combating and/or prophylaxis of skin aging caused by oxidative stress and inflammatory reactions are within the scope of the present invention. The use of carboxylic acid-substituted idebenone derivatives as antioxidants for the stabilization of cosmetic or dermatological compositions, which contain as additive either vitamin A and/or its derivatives (for example, all-E-retinoic acid, 9-Z-retionois acid, 13-Z-retinoic acid, retinal, retinal ester), vitamin B and/or its derivatives, vitamin C and/or its derivatives and vitamin E and/or its derivatives (for example, alpha-tocopherol acetate) individually or in combination, is thus likewise within the scope of the present invention. The stabilizing effect of the present invention relates to both smell and color and in particular to the active ingredient content of the composition.

Further, the use of carboxylic acid-substituted idebenone derivatives as an agent for supporting vesicular breathing and stabilization of mitochondrial membranes with additional anti-apoptotic effect in skin cells and its use for the regeneration and revitalization of aging, stressed or damaged skin, is within the scope of the present invention.

The cosmetic or dermatological compositions of the invention may be conventionally prepared and then used to provide treatment, care, and cleansing of the skin, and as a make-up product in decorative cosmetics. For administration, the carboxylic acid-substituted idebenone derivatives of the invention may be topically applied to the skin in cosmetic and dermatological compositions of the invention in the manner conventional for cosmetics.

Cosmetic and dermatological compositions of the invention may exist in various forms. Hence, they may be, for example, a solution, a serum, an anhydrous preparation, an emulsion or microemulsion of the type water-in-oil (W/O) or of the type oil-in-water (O/W), a multiple emulsion, for example of the type water-in-oil-in-water (W/O/W), a gel, a solid stick, an ointment or an aerosol. It is also advantageous to administer carboxylic acid-substituted idebenone derivatives in encapsulated form, for example in collagen matrices and other conventional encapsulation materials, for example as cellulose encapsulations, in gelatin, wax matrices or liposomally encapsulated.

It is also possible and advantageous within the scope of the present invention to add carboxylic acid-substituted idebenone derivatives to aqueous systems or surfactant compositions for cleansing the skin.

The use of carboxylic acid-substituted idebenone derivatives for the protection of the skin from oxidative stress is also regarded as an advantageous embodiment of the present invention, in particular the use of carboxylic acid-substituted idebenone derivatives in washing formulations.

The cosmetic and dermatological compositions of the invention may contain cosmetic auxiliaries, as are used conventionally in such compositions, for example preservatives, bactericides, perfumes, substances for preventing foaming, dyestuffs, pigments which have a coloring effect, thickening agents, surfactant substances, emulsifiers, softening, moisturizing and/or moisture-retaining substances, fats, oils, waxes or other conventional constituents of a cosmetic or dermatological formulation, such as alcohols, polyols, polymers, foam stabilizers, electrolytes, organic solvents or silicone derivatives.

In particular, carboxylic acid-substituted idebenone derivatives may also be combined according to the invention with other antioxidants and/or free radical absorbers. All antioxidants which are suitable or conventional for cosmetic and/or dermatological applications may be used according to the invention as favorable antioxidants. The antioxidants are advantageously selected from the group consisting of resveratrol, amino acids (e.g., glycine, histidine, tyrosine, tryptophan) and their derivatives, imidazoles (e.g., urocanic acid) and their derivatives, peptides, such as D,L-carnosine, D-carnosine, L-carnosine and their derivatives (e.g., anserine), carotinoids, carotenes (e.g., alpha-carotene, beta-carotene, lycopene) and their derivatives, chlorogenic acid and its derivatives, lipoic acid and its derivatives (e.g., dihydrolipoic acid), aurothioglucose, propylthiouracil and other thiols (e.g., thioredoxin, glutathione, cysteine, cystine, cystamine and their glycosyl, N-acetyl, methyl, ethyl, propyl, amyl, butyl and lauryl, palmitoyl, oleyl, gamma-linoleyl, cholesteryl and glyceryl esters) and their salts, dilauryl thiodipropionate, distearyl thiodipropionate, thiodipropionic acid and their derivatives (esters, ethers, peptides, lipids, nucleotides, nucleosides and salts) and sulphoximine compounds (e.g., buthionine sulphoximines, homocysteine sulphoximine, buthionine sulphones, pentathionine sulphoximine, hexathionine sulphoximine, heptathionine sulphoximine) in very low, acceptable doses (e.g., pmole to µmmoles/kg), also (metal) chelating agents (e.g., alpha-hydroxy fatty acids, palmitic acid, phytic acid, lactoferrin), alpha-hydroxy acids (e.g., citric acid, lactic acid, malic acid, mandelic acid), humic acid, colic acid, colic extracts, bilirubin, biliverdin, EDTA, EGTA and their derivatives, unsaturated fatty acids and their derivatives (e.g., gamma-linolenic acid, linolic acid, oleic acid), folic acid and their derivatives, ubiquinone and ubiquinol and their derivatives, vitamin C and derivatives (e.g., ascorbyl palmitate, Mg-ascorbyl phosphate, ascorbyl acetate), tocopherols and derivatives (e.g., vitamin E acetate), vitamin A and derivatives (e.g., vitamin A palmitate) and coniferyl benzoate of benzoin resin, rutinic acid and their derivatives, butylhydroxy toluene, butylhydroxy anisole, nordihydroguaiacic acid, nordihydroguaiaretic acid, trihydroxybutyrophenone, uric acid and its derivatives, mannose and its derivatives, sesamol, sesamolin, zinc and its derivatives (e.g., ZnO, $ZnSO_4$), selenium and its derivatives (e.g., selenium methionine), stilbenes and their derivatives (e.g., stilbene oxide, trans-stilbene oxide, resveratrol) and the suitable derivatives of the invention (salts, esters, ethers, sugars, nucleotides, nucleosides, peptides and lipids) of these said active ingredients.

The quantity of the aforementioned antioxidants (one or more compounds) in the compositions may be 0.0001 wt % to 30 wt %, preferably 0.05 wt % to 20 wt %, more preferably 1-10 wt %, based on the total weight of the composition.

Provided vitamin E, resveratrol, and/or their derivatives represent the additional antioxidant(s), it is advantageous to select their particular concentration from the range from 0.0001-20 wt %, based on the total weight of the composition.

Provided vitamin A or vitamin A derivatives or carotenes or their derivatives represent the additional antioxidant(s), it is advantageous to select their particular concentrations from the range from 0.0001-10 wt %, based on the total weight of the composition.

Emulsions according to the present invention are advantageous and contain, for example the afore-mentioned fats, oils, waxes and other adipoids, and water and an emulsifier, as is used conventionally for such a type of formulation.

The lipid phase may advantageously be selected from the following substance group: mineral oils, mineral waxes; oils, such as triglycerides of capric or caprylic acid, also natural oils, such as for example castor oil; fats, waxes and other natural and synthetic adipoids, preferably esters of fatty acids with alcohols of low C number, for example with isopropanol, propylene glycol or glycerine, or esters of fatty alcohols with alkane acids of low C number or with fatty acids; alkyl benzoates; silicone oils, such as dimethylpolysiloxanes, diethylpolysiloxanes, diphenylpolysiloxanes and mixtures thereof.

The oil phase of the emulsions, oleogels or hydrodispersions or lipodispersions within the scope of the present invention is advantageously selected from the group of esters of saturated and/or unsaturated, branched and/or unbranched alkane carboxylic acids of chain length from 3 to 30 C atoms and saturated and/or unsaturated, branched and/or unbranched alcohols of chain length from 3 to 30 C atoms, from the group of esters from aromatic carboxylic acids and saturated and/or unsaturated, branched and/or unbranched alcohols of chain length from 3 to 30 C atoms. Such ester oils may then advantageously be selected from the group isopropyl myristate, isopropyl palmitate, isopropyl stearate, isopropyl oleate, n-butyl stearate, n-hexyl laurate, n-decyloleate, isooctyl stearate, isononyl stearate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate, erucyl erucate and synthetic, semi-synthetic, and natural mixtures of such esters, for example jojoba oil.

Furthermore, the oil phase may advantageously be selected from the group of branched and unbranched hydrocarbons and waxes, silicone oils, dialkyl ethers, the group of saturated or unsaturated, branched or unbranched alcohols, and fatty acid triglycerides, namely the triglycerine esters of saturated and/or unsaturated, branched and/or unbranched alkane carboxylic acids of chain length from 8 to 24, in particular 12-18, C atoms. The fatty acid triglycerides may advantageously be selected, for example from the group of synthetic, semi-synthetic and natural oils, for example olive oil, sunflower oil, soybean oil, peanut oil, rape-seed oil, almond oil, palm oil, coconut oil, palm kernel oil and the like.

Also any mixtures of such oil and wax components can be used advantageously within the scope of the present invention. It may also optionally be advantageous to use waxes, for example cetyl palmitate, as the single lipid component of the oil phase.

The oil phase is advantageously selected from the group 2-ethylhexyl isostearate, octyl dodecanol, isotridecyl isononanoate, isoeicosane, 2-ethylhexyl cocoate, $C_{12-15}$ alkyl benzoate, capryl-capric acid triglyceride, dicaprylyl ether.

Mixtures of $C_{12-15}$ alkyl benzoate and 2-ethylhexyl isostearate, mixtures of $C_{12-15}$ alkyl benzoate and isotridecyl isononanoate and mixtures of $C_{12-15}$ alkyl benzoate, 2-ethylhexyl isostearate and isotridecyl isononanoate are particularly advantageous.

Of the hydrocarbons, paraffin oil, squalane and squalene can be used advantageously within the scope of the present invention.

The oil phase may advantageously also contain cyclic or linear silicone oils or may consist completely of such oils, but wherein it is preferable, apart from the silicone oil or the silicone oils, to use an additional amount of other oil phase components.

Cyclomethicone (octamethylcyclotetrasiloxane) is advantageously employed as silicone oil to be used according to the invention. However, other silicone oils should also advantageously be used within the scope of the present invention, for example hexamethylcyclotrisiloxane, polydimethylsiloxane, poly(methylphenylsiloxane).

Mixtures of cyclomethicone and isotridecyl isononanoate, of cyclomethicone and 2-ethylhexyl isostearate, are also particularly advantageous.

The aqueous phase of the compositions of the invention may optionally contain advantageously alcohols, diols or polyols of low C number, and their ethers, preferably ethanol, isopropanol, propylene glycol, glycerine, ethylene glycol, ethylene glycol monoethyl or monobutyl ether, propylene glycol monomethyl, monoethyl or monobutyl ether, diethylene glycol monomethyl or monoethyl ether and analogous products, also alcohols of low C number, for example ethanol, isopropanol, 1,2-propane diol, glycerine and in particular one or more thickening agents, which may advantageously be selected from the group silicon dioxide, aluminum silicates, polysaccharides or their derivatives, for example hyaluronic acid, xanthan gum, hydroxypropylmethylcellulose, particularly advantageously from the group of polyacrylates, in each case individually or in combination.

Mixtures of the above-mentioned solvents are used in particular. For alcoholic solvents, water may be a further constituent.

Gels according to the present invention conventionally contain alcohols of low C number, for example ethanol, isopropanol, 1,2-propane diol, glycerine and water or an above-mentioned oil in the presence of a thickening agent, which for oily-alcoholic gels is preferably silicon dioxide or an aluminum silicate, for aqueous-alcoholic or alcoholic gels is preferably a polyacrylate.

The conventionally-known, highly volatile, liquefied propellants, for example hydrocarbons (propane, butane, isobutane), which may be used alone or mixed with one another, are suitable as propellants for compositions which can be sprayed from aerosol containers according to the present invention: Compressed air can also advantageously be used.

Compositions according to the present invention may also advantageously contain substances which absorb UV radiation in the UVB range, wherein the total quantity of filter substances is, for example 0.1 wt % to 30 wt %, preferably 0.5 to 10 wt %, more preferably 1.0 to 6.0 wt %, based on the total weight of the compositions, in order to provide cosmetic compositions which protect the skin from the entire range of ultraviolet radiation. They may also serve as sunscreen agents for the skin.

If the compositions according to the present invention contain UVB filter substances, they may be oil-soluble or water-soluble. According to the invention, advantageous oil-soluble UVB filters are, for example: mineral oils, mineral waxes; oils, such as triglycerides of capric or caprylic acid, also natural oils, such as for example castor oil; fats, waxes and other natural and synthetic adipoids, preferably esters of fatty acids with alcohols of low C number, for example with isopropanol, propylene glycol or glycerine, or esters of fatty alcohols with alkane acids of low C number or with fatty acids; alkyl benzoates; silicone oils, such as dimethylpolysiloxanes, diethylpolysiloxanes, diphenylpolysiloxanes and mixtures thereof. 3-benzylidene camphor derivatives, preferably 3-(4-methylbenzylidene)camphor, 3-benzylidene camphor; 4-aminobenzoic acid derivatives, preferably (2-ethylhexyl)4-(dimethylamino)benzoate, amyl 4-(dimethylamino)benzoate; esters of cinnamic acid, preferably (2-ethylhexyl) 4-methoxycinnamate, isopentyl 4-methoxycinnamate; esters of salicylic acid, preferably (2-ethylhexyl)salicylate, (4-isopropyl-benzyl)salicylate, homomentyl salicylate, derivatives of benzophenone, preferably 2-hydroxy-4-methoxybenzophenone, 2-hy-droxy-4-methoxy-4'-methylbenzophenone, 2,2'-dihydroxy-4-methoxybenzophenone; esters of benzylidenemalonic acid, preferably di(2-ethylhexyl) 4-methoxybenzylidenemalonate, -2,4,6-trianilino(p-carbo-2'-ethyl-1'hexyloxy)-1,3,5-triazine.

Advantageous water-soluble UVB filters are, for example: salts of 2-phenylbenzimidazole-5-sulphonic acid, such as its sodium, potassium or its triethanol-ammonium salt, and the sulphonic acid itself; sulphonic acid derivatives of benzophenones, preferably 2-hydroxy-4-methoxybenzophenone-5-sulphonic acid and their salts; sulphonic acid derivatives of 3-benzylidene camphor, such as for example 4-(2-oxo-3-bornylidene-methyl)benzene sulphonic acid, 2-methyl-5-(2-oxo-3-bornylidene-methyl)sulphonic acid and their salts as well as 1,4-di(2-oxo-10-sulpho-3-bornylidene-methyl)benzene and its salts (the corresponding 10-sulphato compounds, for example the corresponding sodium, potassium or triethanol; -ammonium salt), also designated as benzene-1,4-di(2-oxo-1-bornylidene-methyl)-10-sulphonic acid.

The list of the said UVB filters, which may be used in combination with the active ingredient combinations of the present invention, should not be limiting.

Also within the scope of the present invention is the use of a combination of carboxylic acid-substituted idebenone derivatives with at least one UVB filter as antioxidant or the use of a combination of carboxylic acid-substituted idebenone derivatives with at least one UVB filter as antioxidant in a cosmetic or dermatological composition.

It may also be advantageous to combine carboxylic acid-substituted idebenone derivatives with UVA filters, which hitherto are conventionally present in cosmetic compositions. These substances are preferably derivatives of dibenzoylmethane, in particular 1-(4'-tert.butylphenyl)-3-(4'-methoxyphenyl)propane-1,3-dione and 1-phenyl-3-(4'-isopropylphenyl)propane-1,3-dione. These combinations or compositions which contain these combinations are also an object of the invention. The quantities used for the UVB combination may be used.

Also within the scope of the present invention is the use of a combination of carboxylic acid-substituted idebenone derivatives with at least one UVA filter as antioxidant or the use of a combination of the active ingredient combinations of the invention with at least one UVA filter as antioxidant in a cosmetic or dermatological composition.

Also within the scope of the present invention is the use of a combination of carboxylic acid-substituted idebenone derivatives with at least one UVA filter and at least one UVB filter as antioxidant or the use of a combination of carboxylic acid-substituted idebenone derivatives with at least one UVA filter and at least one UVB filter as antioxidant in a cosmetic or dermatological composition.

Cosmetic and dermatological compositions having an effective amount of carboxylic acid-substituted idebenone derivatives may also contain inorganic pigments, which are used conventionally in cosmetics to protect the skin from UV rays. They are oxides of titanium, zinc, zirconium, silicon, manganese, cerium and mixtures thereof, and modifications in which the oxides are the active agents. They are particularly preferably pigments based on titanium dioxide.

These combinations of UVA filters and pigment or compositions containing this combination are also within the scope of the present invention. The quantities mentioned for the above combinations may be used.

Cosmetic compositions which are a skin-cleansing agent or shampooing agent preferably contain at least one anionic, non-ionic or amphoteric surfactant substance, or also mixtures of such substances, carboxylic acid-substituted idebenone derivatives in aqueous medium and auxiliaries, as are used conventionally therefore. The surfactant substance or the mixtures of these substances may be present in the shampooing agent in a concentration between 1 wt % and 50 wt %.

These cosmetic or dermatological compositions may also be aerosols having the auxiliaries conventionally used therefor.

Aqueous cosmetic cleansing agents of the invention or low-water or anhydrous cleansing agent concentrates intended for aqueous cleansing may contain anionic, non-ionic and/or amphoteric surfactants, for example traditional soaps, for example fatty acid salts of sodium alkyl sulphates, alkyl ether sulphates, alkane and alkyl benzene sulphonates sulphoacetates sulphobetaines sarcosinates amidosulphobetaines sulphosuccinates sulphosuccinic acid semi-esters alkyl ether carboxylates protein-fatty acid condensates alkylbetaines and amidobetaines fatty acid alkanol amides polyglycol ether derivatives.

Cosmetic compositions which are cosmetic cleansing compositions for the skin, may be present in liquid or solid form. In addition to carboxylic acid-substituted idebenone derivatives, they preferably contain at least one anionic, non-ionic or amphoteric surfactant substance or mixtures thereof, if required one or more electrolytes and auxiliaries, as are used conventionally therefor. The surfactant substance may be present in the cleansing compositions in a concentration between 0.001 and 99.999 wt %, based on the total weight of the compositions.

Cosmetic compositions which are a shampooing agent, in addition to a effective amount of carboxylic acid-substituted idebenone derivatives, preferably contain an anionic, non-anionic or amphoteric surfactant substance or mixture thereof, optionally an electrolyte of the invention and auxiliaries, as are used conventionally therefor. The surfactant substance may be present in the shampooing agent in a concentration between 0.001 wt % and 99.999 wt %.

The compositions according to the present invention contain, apart from the afore-mentioned surfactants, water and optionally the additives which are conventional in cosmetics, for example perfume, thickener, dyestuffs, deodorants, antimicrobial materials, back-fatting agents, complexing and sequestering agents, pearlescent agents, plant extracts, vitamins and/or their derivatives, active ingredients and the like.

The present invention also includes a cosmetic process for protecting the skin and the hair from oxidative or photooxidative processes, which is characterized in that a cosmetic agent, which contains an effective concentration of carboxylic acid-substituted idebenone derivatives, is applied to the skin or hair in adequate quantity.

Likewise, the present invention also includes a process for protecting cosmetic or dermatological compositions from oxidation or photo-oxidation, wherein these compositions, for example compositions for treating and caring for the hair are, in particular hair lacquers, shampooing agents, also make-up products, such as for example nail varnishes, lipsticks, foundations, washing and showering compositions, creams for treating or caring for skin or other cosmetic compositions, the constituents of which may bring with them stability problems due to oxidation or photo-oxidation on storage, characterized in that the cosmetic compositions have an effective amount of carboxylic acid-substituted idebenone derivatives.

The quantity of carboxylic acid-substituted idebenone derivatives in these compositions may be 0.0001-30 wt %, preferably 0.05-5 wt %, more preferably 0.1-2.0 wt %, based on the total weight of the compositions.

Also within the scope of the present invention are processes for producing the cosmetic agents of the invention, which is characterized in that active ingredient combinations of the invention are incorporated into cosmetic and dermatological formulations in a manner known to one of skill in the art.

EXAMPLES

The use of these and other examples anywhere in the specification is illustrative only, and in no way limits the scope and meaning of the invention or of any exemplified form. Likewise, the invention is not limited to any particular preferred embodiments described herein. Indeed, modifications and variations of the invention may be apparent to those skilled in the art upon reading this specification, and can be made without departing from its spirit and scope. The invention is therefore to be limited only by the terms of the appended claims, along with the full scope of equivalents to which the claims are entitled.

Example 1

Synthesis of Idebenone Dipalmitoyl Glycerate

This example provides a synthesis of 3-oxo-3-(9-(2,4,5-trimethyl-3,6-dioxocyclohexa-1,4-dienyl)monyloxy)propane-1,2-diyl dipalmitate (Compound 5; idebenone dipalmitoyl glycerate), which is representative of the carboxylic acid-substituted idebenone derivatives of the present invention.

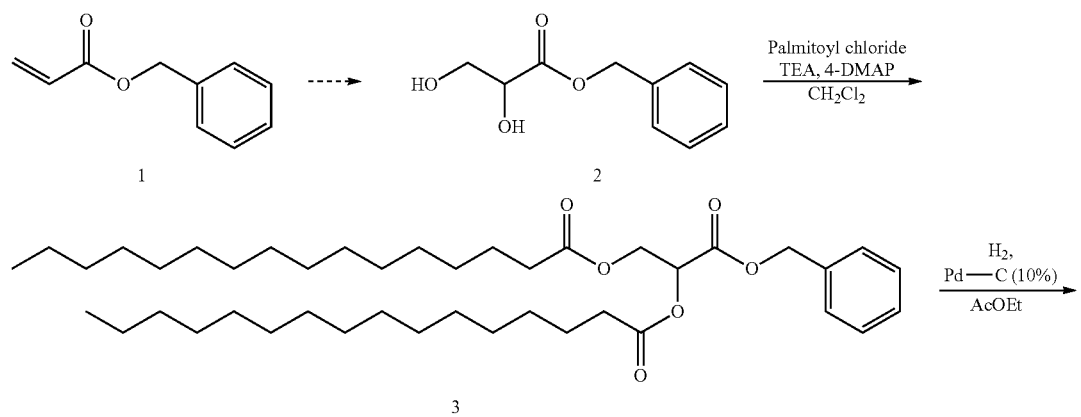

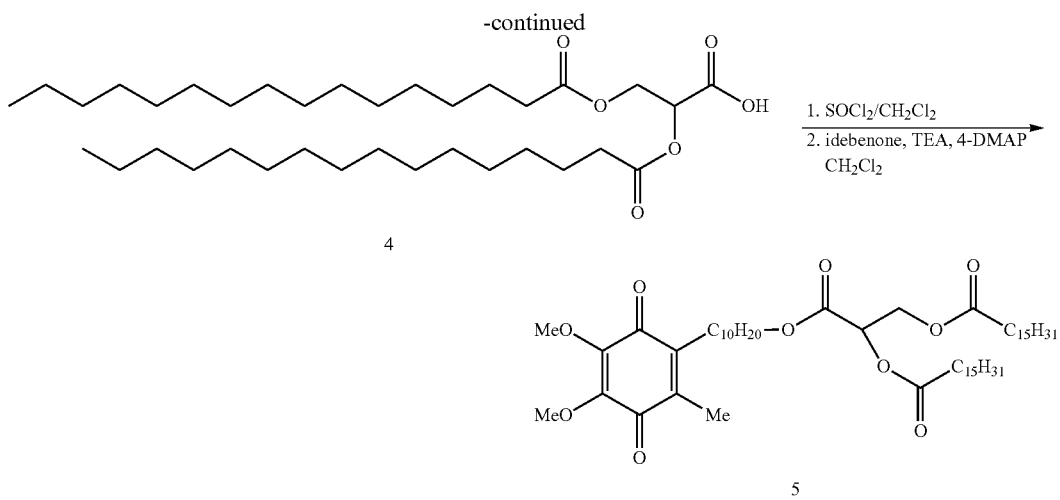

A starting material in the idebenone dipalmitoyl glycerate synthesis is benzyl acrylate (Compound 1), which may be subjected to various chemical reactions in order to form a crude diol oil (Compound 2). This diol is then subjected to an acylation reaction with palmitoyl chloride in the presence of various reagents (TEA, 4-DMAP, and $CH_2Cl_2$) in order to form a tri-ester, Compound 3. This product is then reacted with ethyl acetate (AcOEt) in the presence of various reagents ($H_2$ and Pd—C (10%)) to form an acid, Compound 4. Then, Compound 4 is combined with a solvent ($SOCl_2/CH_2Cl_2$) and reacted with idebenone in the presence of various reagents (TEA, 4-DMAP, and $CH_2Cl_2$) to form the end product, Compound 5 (idebenone dipalmitoyl glycerate).

The dihydroxylation of benzyl acrylate (Compound 1) to form Compound 2 may be performed in various ways. One method is to react benzyl acrylate (1.0 mmol) with 0.4 mol % of potassium osmate dihydrate, three equivalents of potassium ferricyanate (III), and three equivalents of potassium carbonate in a 1:1 mixture of t-butanol and water. (*Angew. Chem. Int. Ed. Engl.* 1996, 35, 448-451). Stir the reaction at room temperature for approximately 21 hours. It may be necessary to add more of the osmate catalyst to drive the reaction to completion. After an aqueous workup, the crude diol (Compound 2) is obtained in an almost quantitative yield.

Another method for dihydroxylation of benzyl acrylate is to use non-volatile potassium osmate dihydrate. (*J. Org. Chem.* 1998, 6094). Benzyl acrylate (1.0 mmol) was reacted with 0.5 mol % of potassium osmate dihydrate, 1.3 equivalents of N-methylmorpholine N-oxide (NMO) in a 1:1:1 solvent mixture of water:acetone:acetonitrile at room temperature. The reaction was complete in 12 hours. After an aqueous workup, the crude diol (Compound 2) was obtained as an oil in nearly quantitative yield. The proton NMR indicated that the crude diol was ~95% pure. This crude oil became dark brown after standing overnight at room temperature. Probably a small amount of residual osmate was present in the crude diol and was responsible for the color change. The work-up conditions may be modified to include a bisulfite wash and/or a plug filtration to move any baseline impurities. If the darkening cannot be eliminated, the crude diol (Compound 2) may be taken directly on to the tri-ester (Compound 3) and purified at the acid stage of Compound 4.

The crude oil was purified by column chromatography to identify the diol (Compound 2). This compound did not ionize with electrospray LC/MS. The proton NMR confirmed the desired product, Compound 2, had been prepared.

Example 2

Compositions Containing Compounds of the Present Invention

Compositions containing carboxylic acid-substituted idebenone derivatives of the present invention should preferably be free of sensitizing agents (e.g., paraben). Suitable compositions according to the present invention may be prepared with various ingredients, as described below. The "CA-Sub Idebenone Derivative" referenced in each composition in this example refers to a carboxylic acid-substituted idebenone derivative of the present invention, such as idebenone dipalmitoyl glycerate.

Facial Cleanser of the present invention containing: Aqua, Sodium Lauroyl Oat Amino-Acids, Sodium C12-16 Olefin Sulfonate, Cocamidopropylamine Oxide, Sodium Lactate, PEG-6 Caprylic/Capric Glycerides, Sucrose Polysoyate, PEG-6 Lauramide, Lactic Acid, CI 77891, Glycerin, Glycol Palmitate, Cetearyl Alcohol, Ceteareth-33, CA-Sub Idebenone Derivative, Salicylic Acid, Caprylic/Capric Triglyceride, Coco-Glucoside, Coconut Alcohol, *Cucumis Sativus* Fruit Extract, PEG-120 Methyl Glucose Dioleate, Hydroxyethylcellulose, Aluminum Hydroxide, Stearic Acid, Xanthan Gum, Citric Acid, Disodium EDTA, and Phenoxyethanol.

Eye Serum of the present invention containing. Aqua, Sodium Lactate, Isopropyl Lauroyl Sarcosinate, PPG-3 Benzyl Ether Myristate, Algae Extract, CI-77891, Glycerin, Palmitoyl Tripeptide-3, Glycerine, Lactic Acid, Decene/Butene Copolymer, Caffeine, CA-Sub Idebenone Derivative, Retinol, Chondrus Crispus, Phenyl Trimethicone, Cyclopentasiloxane, Phospholipids, Dimethiconol, Xanthan Gum, Glucose, Aluminum Hydroxide, Hydrated Silica, Alginic Acid, CI-77489, Silica, Sodium Polyacrylate, PVM/MA Copolymer, Cetearyl Olivate, Sorbitan Olivate, C20-22 Alkyl Phosphate, C20-22 Alcohols, Polysorbate 20, Acrylamide/Sodium Acryloyldimethyl Taurate Copolymer, Isohexadecane, Polysorbate 80, Hydroxyethylcellulose, Triethanolamine, Disodium EDTA, and Phenoxyethanol.

Moisturizing Facial Cream of the present invention containing: Aqua, Sodium Lactate, Caprylic/Capric Triglyceride, Bis-Hydroxyethoxypropyl Dimethicone, Glycerin, Isopropyl Lauroyl Sarcosinate, Lactic Acid, Cetearyl Glucoside, Glycine Soja Protein, Oxido Reductases, CA-Sub Idebenone Derivative, Retinol, Sodium Hyaluronate, Sodium PCA, Urea, Trehalose, Chondrus Crispus, Glucose, Isohexadecane, Polyquaternium-51, Sodium Polyacrylate, PVM/MA Copolymer, Xanthan Gum, Cetearyl Olivate, Sorbitan Olivate, Glyceryl Stearate, PEG-100 Stearate, Polysorbate 20, Acrylamide/Sodium Acryloyldimethyl Taurate Copolymer, Polysorbate 80, Hydroxyethylcellulose, Magnesium Aluminum Silicate, Steareth-100, CI-77891, Hydrogenated Glyceridic Oil, Disodium EDTA, and Phenoxyethanol.

Treatment Peel of the present invention containing: Lactic Acid, Aqua, SD Alcohol 40-B, Ammonium Lactate, Salicylic Acid, CA-Sub Idebenone Derivative, and Hydroxyethylcellulose.

Alternative composition (e.g., cream) of the present invention containing: Aqua, Glycerin, Cetyl Ricinoleate, Isohexadecane, Ceresin, Glyceryl Stearate, Isopropyl Lauroyl Sarcosinate, Sericin, Dimethicone, PEG-60 Hydrogenated Castor Oil, Steareth-2, Sodium PCA, PEG-100 Stearate, CI-77891, CA-Sub Idebenone Derivative, Cholesterol, Ceramide III, Linoleic Acid, Linolenic Acid, Tocopherol, *Panicum Miliaceum* Extract, Glycosaminoglycans, BHT, Propylene Glycol, Styrene Acrylates Copolymer, Hydrolyzed Corn Starch, Ammonium Hydroxide, PEG-30 Dipolyhydroxystearate, Cetyl Hydroxyethylcellulose, Xanthan Gum, Magnesium Aluminum Silicate, Disodium EDTA, and Phenoxyethanol.

Alternative composition (e.g., cream) of the present invention containing: Aqua, Sodium Lactate, Glycerin, Sucrose Cocoate, Lactic Acid, Isohexadecane, Isopropyl Lauroyl Sarcosinate, Glyceryl Stearate, PEG-100 Stearate, Sorbitan Stearate, Steareth-2, CI-77891, Magnesium Aluminum Silicate, PEG-60 Hydrogenated Castor Oil, Butylene Glycol, Methyl Dihydroxybenzoate, CA-Sub Idebenone Derivative, Retinol, Tocopherol, Glycyrrhiza Glabra Root Extract, Moms Alba Leaf Extract, Camellia Oleifera Leaf Extract, *Vitis Vinifera* Extract, Magnesium Ascorbyl Phosphate, BHT, Bisabolol, Allantoin Glycyrrhetinic Acid, Dimethicone, Polysorbate 20, PEG-30 Dipolyhydroxystearate, Xanthan Gum, Cetyl Hydroxyethylcellulose, Disodium EDTA, Propylene Glycol, Styrene Acrylates Copolymer, Hydrolyzed Corn Starch, Ammonium Hydroxide, and Phenoxyethanol.

Sun Protector of the present invention containing: Zinc Oxide, Octinoxate, Oxybenzone, Octisalate, Aqua, Dicaprylyl Carbonate, PEG-20 Stearate, CA-Sub Idebenone Derivative, Pentylene Glycol, Glyceryl Stearate, Laureth-23, Silica, Bis-Hydroxyethoxypropyl Dimethicone, Cetearyl Alcohol, Coco-Glucoside, Butyrospermum Parkii Extract, Phospholipids, Cyclopentasiloxane, Cyclohexasiloxane, Butylene Glycol, Caprylic/Capric Triglyceride, Ascorbyl Tetraisopalmitate, Tocopherol, Carbomer, Sodium DNA, Cetyl Hydroxyethylcellulose, Potassium Cetyl Phosphate, Hydrogenated Palm Glycerides, Dimethoxydiphenylsilane/Triethoxycaprylylsilane Crosspolymer, Xanthan Gum, Disodium EDTA, Diazolidinyl Urea, and Iodopropynyl Butylcarbamate.

Environmental Protector of the present invention containing: Aqua, Glycerin, Dipropylene Glycol, Glyceryl Stearate, PEG-100 Stearate, Stearyl Alcohol, Ceteareth-20, CA-Sub Idebenone Derivative, Superoxide Dismutase, Cetyl Hydroxyethylcellulose, Xanthan Gum, Disodium EDTA, and Phenoxyethanol.

Prophetic Composition (e.g., body cream) of the present invention containing at least: CA-Sub Idebenone Derivative, Resveratrol, Xanthin (e.g., Caffeine), AHA (Lactic Acid), and Stimulators of Collagen Synthesis (as, e.g., Vitamin C and derivatives thereof).

Example 3

Maximization Test of Idebenone Dipalmitoyl Glycerate

A study was performed to evaluate the contact-sensitizing potential of a topical Facial Cream containing idebenone dipalmitoyl glycerate (Vehicle+1% idebenone dipalmitoyl glycerate) using the Maximization Test. The test was a repeat insult patch test wherein the test material was applied under an occlusive dressing to the upper outer arm, volar forearm or back repeatedly to the same site for five 48-hour induction periods, followed 10-14 days later by a single challenge to a naive skin site. The test sample was coded Cream A and tested as supplied viz. neat. All test materials were stored under ambient conditions in an inaccessible location under the supervision of the investigator.

The test subjects were all healthy, adult volunteers over the age of 18 years. None of the subjects had a medical or dermatological illness and none were sensitive to sunlight or to topical preparations and/or cosmetics. The criteria for exclusion were: history of sun hypersensitivity and photosensitive dermatoses; history of allergy or hypersensitivity to cosmetics, toiletries or other dermatological products; history of recurrent dermatological diseases, e.g., psoriasis, atopic eczema; pregnancy or mothers who were breastfeeding; scars, moles or other blemishes over the upper arm(s), volar forearm(s) or back which could have interfered with the study; history of recurrent urticaria or hives; subjects who were receiving systemic or topical drugs or medications which could interfere with delayed immunologic responses e.g., corticosteroids; history of allergies to the test product or components in the test product; other conditions considered by the investigator as sound reasons for disqualification from enrollment into the study.

The patch was applied to the upper outer arm, volar forearm or the back of each subject. The entire test was composed of two distinct phases: an Induction phase and a Challenge phase.

Induction Phase: Approximately 0.05 ml of aqueous SLS (0.25%) was applied to a designated site under a 15 mm disc of Webril cotton cloth and the patch was fastened to the skin with occlusive tape for a period of 24 hours. After 24 hours, the SLS patch was removed and 0.05 ml of the test material was applied to the same site before the site was again covered with occlusive tape (induction patch). The induction patch was left in place for 48 hours (or for 72 hours when placed over a weekend) after which it was removed and the site again examined for irritation. If no irritation was present, a 0.25% aqueous SLS patch was again reapplied to the same site for 24 hours, followed by reapplication of a fresh induction patch with the test material to the same site. This sequence viz. 24 hour SLS pre-treatment followed by 48 hours of test material application was continued for a total of 5 induction exposures. If irritation developed at any time-point during the induction phase as previously outlined, the 24-hour SLS pre-treatment patch was eliminated and only the test material was reapplied to the same site after a 24-hour rest period during which no patch was applied. The aim during this phase of the study was to maintain at least a minimal degree of irritation in order to enhance penetration through the corneum barrier.

Challenge Phase: After a ten day rest period which follows the last induction patch application, the subjects were challenged with a single application of the test material to a new skin site on the opposite arm, forearm or side of back in order to determine if sensitization had developed. Pre-treatment with SLS was performed prior to challenge. Approximately 0.05 ml of a 5.0% aqueous solution was applied to a fresh skin site under a 15 mm disc of Webril cotton and covered with occlusive tape. The SLS patch was left in place for one hour. It was then removed and the test material was applied to the same site. The challenge patch was then covered by occlusive tape and left in place for 48 hours. After that period, the patch was removed and the site graded 15-30 minutes later and again 24 hours later for any reaction.

Scoring Scale:

0=not sensitized

1=mild sensitization (viz. erythema and a little edema)

2=moderate sensitization (erythema with infiltration, raised, spreading beyond the borders of the patch, with or without vesiculation)

3=strong sensitization (large vesiculo-bullous reaction).

Based on these findings, the number of subjects with positive responses were tabulated for the test material. The test system shown in Table I was used to classify the allergenic potential of the test substance.

TABLE I

| Sensitization Rate | Grade | Classification |
|---|---|---|
| 0-2/25 | 1 | Weak |
| 3-7/25 | 2 | Mild |
| 8-13/25 | 3 | Moderate |
| 14-20/25 | 4 | Strong |
| 21-25/25 | 5 | Extreme |

A total of 27 healthy, adult volunteers of both sexes who satisfied the inclusion criteria were enrolled into this study. There were 21 females and 6 males. Their ages ranged from 21 to 65 years. All 27 subjects completed the study. No adverse or unexpected reactions were seen in any of the panelists during the induction phase.

Results: No instances of contact allergy were recorded in any of the 27 subjects at either 48 or 72 hours after the application of the challenge patches. A successful compound is considered to be a compound that elicits no reaction or response from a subject.

Conclusion: Cream A containing idebenone dipalmitoyl glycerate does not possess a detectable contact-sensitizing potential and hence is not likely to cause contact sensitivity reactions under normal use conditions.

Further, idebenone dipalmitoyl glycerate is representative of the full genus of carboxylic acid-substituted idebenone derivatives encompassed by general Formula I, any one of which (and particularly those containing di-, tri-, or poly-fatty acid chains) would be expected to exhibit analogous efficacy and skin tolerance due, e.g., to their high molecular weight. For instance, idebenone dimyristoyl glycerate, idebenone dioleyl glycerate, idebenone dilinoleyl glycerate, idebenone dieicosapentaenyl glycerate, idebenone dierucyl glycerate, idebenone trimyristoyl trihydroxypropanoate, idebenone trioleyl trihydroxypropanoate, idebenone trilinoleyl trihydroxypropanoate, idebenone trieicosapentaenyl trihydroxypropanoate, and idebenone trierucyl trihydroxypropanoate would all be expected to be highly effective in treating skin changes and providing the added benefits of reduced skin irritation, reduced inflammation, increased skin permeability, increased cell permeability, and slow release therapy. A key structural feature common to all carboxylic acid-substituted idebenone derivatives of Formula I is the presence of two or more carboxylic acids (particularly di-, tri-, or poly-fatty acids) that render the compound more soluble across the stratum corneum lipid bi-layers of the skin, enhance delivery of the active ingredient by enhancing permeability of cell membranes, and provide a slow release therapy as the compound hydrolyzes in the skin.

Example 4

Clinical Evaluation of Idebenone Dipalmitoyl Glycerate

A six-week double-blind clinical evaluation was performed, comparing a control vehicle to idebenone dipalmitoyl glycerate for the treatment of red and brown pigmented skin. Approximately 36 women, ages 40-70 with moderate hyperpigmentation and reddening of the skin were selected to participate in the study. Subjects were randomly assigned to one of three groups. Group I received a product with no idebenone active ingredient (vehicle), Group II received the same vehicle with 0.5% Idebenone (Hydroxydecyl Ubiquinone) added, and Group III received the same vehicle with 0.5% of Idebenone Dipalmitoyl Glycerate added. Subjects were instructed to apply the product twice a day (morning and evening) to the facial area for 6 weeks. Canfield VISIA-CR RBX images were made at baseline and after 6 weeks use and analyzed. Digital and UV photographs were also taken, standardizing distance and positioning of the subjects, pre and post product application.

Based on the expert grading and review of the Canfield VISIA-CR RBX images, 27%, 58%, and 58% of the subjects responded with less redness in Group I, Group II, and Group III, respectively. Similarly, 18%, 67%, 75% of the subjects responded with a decrease in brown pigmentation in Group I, Group II, and Group III, respectively. Thus, idebenone dipalmitoyl glycerate achieved an overall improved effect as compared to underivatized idebenone or underivatized idebenone substituted with a monocarboxylic acid.

Idebenone dipalmitoyl glycerate, tested in Examples 3 and 4, is representative of the full scope of carboxylic acid-substituted idebenone derivatives encompassed by general Formula I. Analogous results, particularly with respect to efficacy and skin tolerance (e.g., not causing contact sensitivity in skin), would be expected if other compounds of Formula I were tested using the same form (i.e., a cream) or a different form (e.g., a lotion or ointment) as that described in Examples 3 and 4.

Example 5

Comparative Clinical Sensitization Testing

Clinical sensitization testing was performed on two idebenone esters having relatively low molecular weights (as compared to the compounds of the present invention)—idebenone linoleate ester and idebenone phosphate ester, the structures of which are shown below:

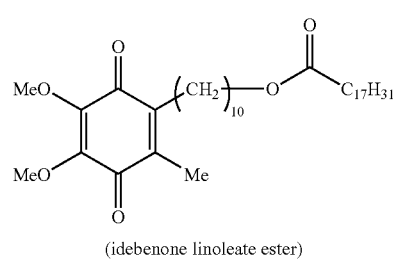

(idebenone linoleate ester)

-continued

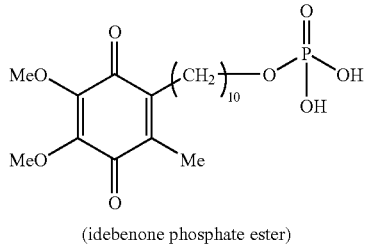

(idebenone phosphate ester)

The same testing protocol described in Example 3 was used in the comparative clinical sensitization tests in this example, but on different panels of subjects.

In the idebenone linoleate ester test (Vehicle+1% idebenone linoleate ester), 25 healthy, adult volunteers of both sexes who satisfied the inclusion criteria were enrolled in the study. All of the subjects completed this study. Results: One subject exhibited a positive reaction—i.e., a recordable level of skin sensitization. Sensitization in even one subject constitutes a failure. Hence, compositions containing idebenone linoleate ester do not possess the added benefits of reduced skin irriation and reduced inflammation, as found in the carboxylic acid-substituted idebenone derivatives of the present invention.

In the idebenone phosphate ester test (Vehicle+1% idebenone phosphate ester), 29 healthy, adult volunteers of both sexes who satisfied the inclusion criteria were enrolled in the study. There were 23 females and 6 males, ranging in age from 19 to 65 years. All of the subjects completed this study. Results: Four subjects exhibited positive reactions i.e., a recordable level of skin sensitization. Since sensitization in even one subject constitutes a failure, compositions containing idebenone phosphate ester do not possess the added benefits of reduced skin irriation and reduced inflammation, as found in the carboxylic acid-substituted idebenone derivatives of the present invention.

Conclusion: The foregoing examples show that the carboxylic acid-substituted idebenone derivatives of the present invention are surprisingly effective compounds for treating skin changes with increased skin tolerance. In particular, these examples and data show that these carboxylic acid-substituted idebenone derivatives have beneficial antioxidant properties and exhibit the particularly advantageous property of increased skin tolerance.

All publications, patents, articles, and other references cited and/or discussed in this specification are incorporated herein by reference in their entirety and to the same extent as if each reference was individually incorporated by reference.

We claim:

1. A method of treating red or brown pigmented skin comprising topically administering a composition comprising a therapeutically effective amount of idebenone dipalmitoyl glycerate to a subject in need thereof.

2. The method of claim 1, wherein the red or brown pigmented skin is caused by UV damage.

3. The method of claim 1, wherein the red or brown pigmented skin comprises erythematous symptoms.

4. The method according to claim 1, wherein the idebenone dipalmitoyl glycerate is present in an amount of 0.1 wt % to 2.0 wt % based on the total weight of the composition.

5. The method according to claim 4, wherein the idebenone dipalmitoyl glycerate is present in an amount of about 0.5% based on the total weight of the composition.

* * * * *